United States Patent [19]

Suciu et al.

[11] Patent Number: 4,496,777

[45] Date of Patent: Jan. 29, 1985

[54] PRODUCTION OF HALOHYDRINS

[75] Inventors: George D. Suciu, Ridgewood; Joon T. Kwon, Freehold Township, Monmouth County; Atef M. Shaban, Nutley, all of N.J.

[73] Assignee: The Lummus Company, Bloomfield, N.J.

[21] Appl. No.: 549,891

[22] Filed: Nov. 9, 1983

[51] Int. Cl.$^3$ ....................... C07C 31/34; C07C 31/36
[52] U.S. Cl. .................................. 568/850; 568/812; 568/821; 568/822; 568/838
[58] Field of Search ............... 568/850, 812, 821, 822, 568/838

[56] References Cited

U.S. PATENT DOCUMENTS 4,008,133  2/1977  Gelbein et al. ...................... 549/521

Primary Examiner—Howard T. Mars
Attorney, Agent, or Firm—Elliot M. Olstein

[57] ABSTRACT

Production of halohydrins; in particular, chlorohydrins by reaction of tertiary alkyl hypohalite and olefinically unsaturated compound in the presence of water and a water soluble salt of an amphoteric metal; in particular, a salt of tin, aluminum, zinc, zirconium, magnesium, or titanium, which provides a pH of from 2 to 5 under reaction conditions.

19 Claims, No Drawings

PRODUCTION OF HALOHYDRINS

This invention relates to the production of halohydrins, and more particularly to the production of chlorohydrins.

U.S. Pat. No. 4,008,133 is directed to the production of epoxy compounds from olefinic compounds, and in such a process, a halohydrin, and in particular, a chlorohydrin is produced by reaction of olefinically unsaturated compound with tertiary alkyl hypochlorite in the presence of water, with the chlorohydrin then being saponified to the olefin oxide.

Japanese Examined Pat. No. 45-4042 (1970) describes the production of chlorohydrins by reaction of olefin, hypochlorite and water in the presence of salts of either a weak acid or a weak base, and discloses as representative examples alkali and ammonium salts. The Japanese patent discloses that such salts act as buffers to maintain a pH in the range of either 2 to 5 or 7 to 9.

The present invention is directed to improving a process for the production of a halohydrin, and in particular a chlorohydrin.

In accordance with the present invention, there is provided a process for producing a halohydrin, and in particular, a chlorohydrin, by reaction of an olefinically unsaturated compound with a tertiary alkyl hypohalite, and in particular, a tertiary alkyl hypochlorite, in the presence of water, wherein the improvement resides in producing the halohydrin in the presence of at least one salt of an amphoteric metal which is dissolved in at least the water to provide a pH of from 2 to 5.

Applicant has found that the use of such salts, and in particular, salts of tin, zirconium, aluminum, titanium, magnesium and zinc, improves the selectivity and productivity of the desired halohydrin.

Although the present invention has broad applicability to the production of halohydrins, the present invention has particular applicability to the production of a chlorohydrin by reaction of a tertiary alkyl hypochlorite with an olefinically unsaturated compound.

The salts which are employed are generally nitrates, sulfates, chlorides, phosphates, bromides, iodides, etc.

The preferred salts of amphoteric metals are those salts which are soluble in at least the aqueous portion under the reaction conditions to provide a salt concentration of at least 1%, by weight.

In general, the salt is employed in an amount which is from 1 to 40 wt. %, and preferably in an amount from 5 to 20 wt. %. The salt is one which is soluble in at least the aqueous portion of the reaction mixture.

The reaction between the olefinically unsaturated compound, tertiary alkyl hypochlorite, and preferably tertiary butyl hypochlorite, in the presence of water, and the noted salts, is preferably conducted at a temperature of from 60° F. to 180° F., and more preferably, at a temperature of from 110° F. to 140° F. The upper temperature is set by the decomposition of the hypohalite, and it is to be understood, in some cases, higher or lower temperatures may be employed. The reaction pressure may be atmospheric, superatmospheric or subatmospheric pressure, with a preferred pressure generally being in the order of from 5 to 40 psig.

In the reaction, in general, the water to organic volume ratio is at least 0.5 to 1, and preferably at least 2 to 1. In most cases, the water to organic volume ratio does not exceed 5 to 1. It is to be understood that higher ratios could be employed, but are generally not necessary.

The hypochlorite and olefin are generally employed in about stochimetric portions so as to maximize utilization of both components. In most cases, in order to ensure complete conversion of the more expensive reagent (generally the hypochlorite), the other reagent is used in a slight excess; e.g., 1% to 5% in excess of stoichimetric requirements. A higher excess may be used, but is generally not necessary.

The reaction system is comprised of one or more fluid phases. The fluid phase(s) may be comprised of a liquid phase; or a liquid and gaseous phase, and the liquid phase may be present as one or two phases. Thus, for example, there may be a separate aqueous and organic liquid phases.

The reaction may be accomplished in either a batch, semi-batch or continuous reaction system, with the choice of a specific system being deemed to be within the scope of those skilled in the art from the teachings herein.

The production of chlorohydrin from olefinically unsaturated compound, hypochlorite and water, as disclosed in U.S. Pat. No. 4,008,133 is preferably effected with a feed which does not contain a chloride in ion concentration in excess of 1 mole per liter and preferably the chloride ion concentration should not exceed 0.1 mole per liter.

In general, in employing tertiary alkyl hypochlorite as one of the reactants in the production of the chlorohydrin, when such hypochlorite has been produced by reaction of chlorine, base and tertiary alkanol, such tertiary alkyl hypochlorite may include some amounts of free chlorine, and such amounts should be maintained as low as possible in order not to generate high amounts of additionally chlorinated byproduct. As disclosed in U.S. Pat. No. 4,008,133, it is preferred to limit the amount of free chlorine so that it does not exceed about 7 moles of chlorine per 100 moles of hypochlorite. It is to be understood that greater amounts of chlorine could be present, but such greater amounts may reduce the yield of desired chlorohydrin.

The chlorohydrin production, in the presence of at least one soluble salt of an amphoteric metal, as hereinabove described, may be conducted in the presence of an inert organic solvent, as disclosed in U.S. application Ser. No. 35,558, filed on May 3, 1979. As disclosed in such application, the presence of the organic solvent facilitates subsequent separation of the chlorohydrin product, and tertiary alkanol byproduct into an organic phase, which can be subsequently separated from an aqueous phase. As representative examples of such inert organic solvent, there may be mentioned chlorinated hydrocarbons such as chlorinated aromatics; e.g., o-dichlorobenzene; chlorinated paraffin such as carbon tetrachloride, chloroform, dichloropropane, etc.; ketones; e.g., methyl ethyl ketone, methyl isobutyl ketone, acetone, and the like. The solvents may be employed alone or as a mixture of two or more thereof.

Thus, in accordance with the present invention, chlorohydrin is produced from olefinically unsaturated compound, tertiary alkyl hypochlorite and water, in the presence or absence of an inert organic solvent, and in the presence of an amphoteric metal salt, as hereinabove described, in order to improve selectivity.

The olefinically unsaturated compound employed as feed in the present process may be any one of a wide variety of olefinically unsaturated compounds, including both monoolefinically and di-olefinically unsaturated compounds. The olefinically unsaturated compounds generally employed as feed are represented by the following structural formula:

$$R_1-CH=CH-R_2$$

wherein $R_1$ and $R_2$ are each separately either hydrogen; alkyl; halo, naphthyl, and phenyl substituted alkyl; phenyl; halo and alkyl substituted phenyl; naphthyl; halo and alkyl substituted naphthyl; alkenyl; halo substituted alkenyl; and $R_1$ and $R_2$ can be linked together to provide a cycloalkene (generally 5 to 10 carbon atoms). The alkyl and alkenyl groups generally have 1 to 6 carbon atoms and the halo group is preferably iodo-, bromo-, or chloro-, most preferably chloro-. As representative examples of the most suitable feedstocks, there may be mentioned: alkenes having from 2 to 6 carbon atoms, preferably 2 to 4 carbon atoms with ethylene and propylene being particularly preferred; styrene; cyclohexane; stilbene; butadiene; chloroprene; allyl chloride; allyl bromide; bromoprene; cyclohexene, and cyclopentene. The chlorohydrin produced in accordance with the invention are represented by the following structural formula:

$$R_1-\underset{\underset{OH}{|}}{\overset{\overset{H}{|}}{C}}-\underset{\underset{Cl}{|}}{\overset{\overset{C}{|}}{C}}-R_2$$

wherein $R_1$ and $R_2$ are as defined above.

The present invention for producing a chlorohydrin has particular applicability to an overall process for producing olefin oxide wherein tertiary butyl or tertiary amyl hypochlorite, preferably tertiary butyl hypochlorite, is produced by reaction between tertiary alkanol, chlorine and aqueous base, with the tertiary alkyl hypochlorite then being reacted with olefinically unsaturated compound and water, in the presence of an amphoteric metal salt, as hereinabove described, to produce chlorohydrin and tertiary alkanol byproduct. The chlorohydrin is saponified to the olefin oxide, and the tertiary alkanol byproduct from the chlorohydrin production step is recycled to the hypochlorite production. Such a process is described, for example, in U.S. Pat. No. 4,008,133, with the present invention providing an improvement in such process by increasing the selectivity and production of chlorohydrin.

The present invention is also applicable to various modifications of the basic process for producing olefin oxide, as described in U.S. application Ser. Nos. 35,557, 35,558, and 35,560, all filed on May 3, 1979.

The invention will be further described with respect to the following examples; however, the scope of the invention is not to be limited thereby:

EXAMPLE 1

A 500 ml teflon-lined pressure vessel provided with stirrer, feed lines, thermocouple and pressure gauge, is used. 100 ml of a water solution containing 10% Al(NO$_3$)$_3$ are placed into the vessel and warmed up to 70° C. Through the two inlets, a stream of allyl chloride and one of tBuOCl are fed simultaneously while maintaining the reaction mixture well stirred. 500 mmoles of allyl chloride and 380 mmoles of t-BuOCl were fed during an 11-minute period. The stirring is continued for an additional 4 minutes. During the entire reaction period the measured pressure was 40 psig.

Analysis of the product indicates complete conversion of the t-BuOCl. The molar selectivities based on t-BuOCl were:

Glycerol Dichlorohydrins 84%, Trichloropropane 9%, ethers and other byproducts 7%.

The pH values of the water phase, before and after the reaction, were 2.1 and 2.8, respectively.

EXAMPLE 2

In the same vessel as used in Example 1, 100 ml of an aqueous solution containing 10% Al$_2$(SO$_4$)$_3$, pH=2.1 were heated to 70° C. Gaseous propylene was used for displacing the air from the space above the liquid after which a propylene pressure of 40 psig was applied and maintained throughout the reaction. A stream of t-BuOCl was fed for 15 minutes while intense stirring was practiced. After 103 mmoles t-BuOCl were introduced, the stirring was continued for an additional 5 minutes. Analysis of the reaction mixture indicates complete conversion of the t-BuOCl. The molar selectivities based on t-BuOCl were:

Propylene chlorohydrins 86%, Dichloropropane 3%, ethers and other byproducts 11%.

The present invention is particularly advantageous in that it is possible to achieve high yields of the desired chlorohydrin. The use of a salt of an amphoteric metal, as hereinabove described, increases the reaction rate which increases reactor productivity.

Numerous modifications and variations of the present invention are possible in light of the above teachings and, therefore, within the scope of the appended claims, the invention may be practiced otherwise than as particularly described.

What is claimed is:

1. A process for producing a chlorohydrin, comprising:
reacting an olefinically unsaturated compound with a tertiary alkyl hypohalite in the presence of water and at least one salt of an amphoteric metal which is dissolved in at least the water to provide a pH of from 2 to 5.

2. The process of claim 1 wherein the amphoteric metal salt is selected from the group consisting of salts of aluminum, magnesium, zinc, tin, zirconium and titanium.

3. The process of claim 2 wherein the salt is dissolved in the water in an amount of at least 1%, by weight.

4. The process of claim 3 wherein the reacting is effected at a temperature of from 60° F. to 180° F.

5. The process of claim 4 wherein the volume ratio of water to organic is at least 0.5:1.

6. The process of claim 3 wherein the salt is an aluminum salt.

7. The process of claim 6 wherein the salt is aluminum sulfate.

8. The process of claim 6 wherein the salt is aluminum nitrate.

9. The process of claim 3 wherein the tertiary alkyl hypohalite is a hypochlorite.

10. The process of claim 9 wherein the hypochlorite is tertiary butyl hypochlorite.

11. The process of claim 3 wherein the reacting is effected in the presence of an inert organic solvent.

12. A process for producing a chlorohydrin, comprising:

reacting allyl chloride, water and tertiary butyl hypochlorite in the presence of at least one salt of an amphoteric metal which is dissolved in at least the water to provide a pH of from 2 to 5.

13. The process of claim 12 wherein the salt is dissolved in the water in an amount of at least 1%, by weight.

14. The process of claim 13 wherein the amphoteric metal salt is selected from the group consisting of salts of aluminum, magnesium, zinc, tin, zirconium and titanium.

15. The process of claim 14 wherein the salt is an aluminum salt.

16. The process of claim 15 wherein the salt is aluminum sulfate.

17. The process of claim 15 wherein the salt is aluminum nitrate.

18. The process of claim 14 wherein the reacting is effected at temperature of from 60° F. to 180° F.

19. The process of claim 14 wherein the salt is dissolved in at least the water in an amount of from 1% to 40%, by weight.

* * * * *